United States Patent [19]
Johnson

[11] Patent Number: 4,910,386
[45] Date of Patent: Mar. 20, 1990

[54] APPARATUS FOR HEATING MEDICAL OR DENTAL INSTRUMENTS

[75] Inventor: Philip C. Johnson, Cincinnati, Ohio

[73] Assignee: Reliance Medical Products, Inc., Cincinnati, Ohio

[21] Appl. No.: 277,304

[22] Filed: Nov. 29, 1988

[51] Int. Cl.[4] .............................................. F24C 7/00
[52] U.S. Cl. ..................................... 219/385; 219/521
[58] Field of Search ............... 219/385, 386, 521, 454, 219/218, 242

[56] References Cited

U.S. PATENT DOCUMENTS

| | | | |
|---|---|---|---|
| Re. 19,089 | 2/1934 | Parker | 219/454 |
| 1,458,127 | 6/1923 | Brown . | |
| 1,717,269 | 6/1929 | Shroyer | 219/454 |
| 1,834,353 | 12/1931 | Shoudy . | |
| 2,059,133 | 10/1936 | Merritt | 219/521 |
| 2,471,884 | 5/1949 | Monnot . | |
| 2,527,101 | 10/1950 | Maddox . | |
| 2,999,145 | 9/1961 | Espenhain . | |
| 3,776,694 | 12/1973 | Leittl . | |
| 3,784,270 | 1/1974 | DeLapp | 219/386 |
| 3,837,270 | 9/1974 | Cooper | 219/386 |
| 3,955,922 | 5/1976 | Moulthrop . | |
| 4,092,138 | 5/1978 | Beitner . | |
| 4,241,290 | 12/1980 | Folland | 219/518 |
| 4,278,870 | 7/1981 | Carleton et al. | 219/219 |
| 4,441,013 | 4/1984 | Masreliez | 219/231 |
| 4,641,015 | 2/1987 | Mayeur | 219/386 |

*Primary Examiner*—Teresa J. Walberg
*Attorney, Agent, or Firm*—Wood, Herron & Evans

[57] ABSTRACT

Apparatus for storing and heating medical or dental examination instruments includes a treatment cabinet having a number of drawers including an instrument drawer located immediately beneath a ledge mounted in the interior of the treatment cabinet. The ledge is formed with a recess within which a heat conductive plate is mounted having heating elements affixed thereto. The heating elements are effective to heat the heat conductive plate, which, in turn, elevates the temperature of the interior of the instrument drawer in excess of the body temperature of a patient. Examination instruments stored within the instrument drawer are heated to the same, elevated temperature in preparation for use in examining a patient.

11 Claims, 1 Drawing Sheet

APPARATUS FOR HEATING MEDICAL OR DENTAL INSTRUMENTS

FIELD OF THE INVENTION

This invention relates to medical or dental treatment cabinets, and, more particularly, to a treatment cabinet having an apparatus which heats at least one drawer of the cabinet so that the temperature of instruments stored therein is elevated above body temperature.

BACKGROUND OF THE INVENTION

Dentists, otolaryngologists and other health care professionals use a variety of instruments in examining the ears, nose, throat, mouth etc. Particularly with reflective instruments such as mirrors, it is desirable to elevate the temperature of the instrument to above body temperature so that the patient's breath does not fog the mirror. It is also desirable to elevate the temperature of various instruments which touch the patient for added comfort and to prevent sudden movements of the patient which might take place in reaction to contact with a cold instrument.

A number of devices have been proposed in the prior art for warming instruments such as mirrors used in the examination of patients. One type of device is a free-standing or self-contained mirror warmer comprising a housing having internal heating elements and an opening for receiving the end of the instrument which mounts the mirror. Units of this general type are disclosed, for example, in Folland U.S. Pat. No. 4,241,290; Carleton et al. U.S. Pat. No. 4,278,870; and Beitner U.S. Pat. No. 4,092,138.

One problem with mirror warmers of the type described above is that these units are free-standing and must be placed atop the treatment cabinet or other furniture in the immediate area of the patient examination chair. This takes up valuable space which otherwise could be used for other equipment necessary for examination of the patient. Another problem with mirror warmers of this type is that only the mirror itself and possibly a portion of the handle of the instrument are heated by the warming device. When the instrument is removed from the mirror warmer, the remainder of the handle acts as a heat sink to draw heat away from the mirror end of the instrument, thus lowering the temperature of the mirror. If the physician or dentist delays using the mirror even for a relatively short period of time, its temperature may have decreased to the point where the mirror would become fogged by the patient's breath.

Another type of apparatus employed in the prior art for warming instruments such as mirrors is a treatment cabinet having a series of lightbulbs or similar heating elements mounted to the back wall of the cabinet, in a space between the drawers and back wall, to increase the overall temperature of the interior of the cabinet within which the instruments are stored. Apparatus of this type have the advantage of keeping the instruments in a closed drawer within the treatment cabinet to avoid contamination, but a number of problems are created.

The use of lightbulbs or other heating elements mounted to the back wall of the cabinet is an extremely inefficient and costly means to heat the interior of a treatment cabinet and the instruments therein. The heat produced by the lights or heating elements must move by conduction or convection along the entire area of the drawer or other part of the cabinet which holds the instruments. In most cases, the entire interior of the cabinet is heated whereas the instruments are usually stored in only a small area therein. This wastes a substantial amount of power and is inefficient in heating instruments located furthest from the back wall of the cabinet.

SUMMARY OF THE INVENTION

It is therefore among the objectives of this invention to provide an apparatus for warming medical or dental instruments for use in examining patients which protects the instruments from atmospheric contamination, which efficiently and economically heats the instruments and which avoids heating the environment surrounding the cabinet.

These objectives are accomplished in an apparatus for warming medical and dental instruments which comprises a cabinet having a plurality of drawers including an instrument storage drawer located beneath a ledge mounted in the interior of the cabinet. A heat conductive plate having first and second surfaces is mounted within a recess formed in the ledge such that its first surface faces the recess and its second surface faces the interior of the instrument storage drawer. One or more heating elements are affixed to the first surface of the heat conductive plate, within the recess in the ledge, which are energized by current from a standard wall outlet. The heating elements are effective to heat the heat conductive plate so that the temperature within the interior of the instrument drawer is elevated above body temperature. In turn, instruments such as mirrors placed in the instrument drawer are heated above body temperature in preparation for use in examining a patient.

In the presently preferred embodiment, the surface area of the heat conductive plate is approximately equal to the interior dimensions of the instrument drawer of the cabinet. Two heating elements are affixed to the heat conductive plate which have a combined power rating sufficient to elevate the temperature of the heat conductive plate to about 145°. With an instrument storage drawer having a height dimension of between 2 and 3 inches, the heat conductive plate is effective to elevate the temperature therein to about 115° F. The instruments placed in such instrument drawer are thus heated to a temperature which is greater than body temperature, but less than that which would cause discomfort to the touch of either the attending physician or dentist, or a patient.

The apparatus of this invention has several advantages over the prior art. The instrument warming apparatus is integrally formed with a treatment cabinet of the type utilized in the examination rooms of dentists and otolaryngologists. The instrument warmer takes up no space atop the treatment cabinet which is needed for other equipment. Moreover, the instruments are stored within a closed drawer which reduces their exposure to any airborne contaminants which may be present in the examination room.

Another advantage of the apparatus herein is that it operates efficiently and economically compared to the prior art. The heating elements and heat conductive plate are located within the treatment cabinet immediately above the interior of the drawer which stores the instruments to be heated. The heat produced by the instrument warmers herein is therefore directly applied to the area which requires heating and only to that area.

In contrast, prior art instrument heating apparatus have employed heating lamps or bulbs mounted to the back wall of the treatment cabinet. The heat output from these bulbs has to be transmitted by convection or conduction throughout the width and depth dimension of an instrument storage drawer in order to effectively heat instruments stored therein. Often, the entire interior of the cabinet is heated by such bulbs, including areas which do not need to be heated. The instant invention is thus far more economical and effective in heating all of the instruments placed within the instrument storage drawer of the treatment cabinet without transmitting an undue amount of heat to other areas of the treatment cabinet.

DESCRIPTION OF THE DRAWINGS

The structure, operation and advantages of the presently preferred embodiment of this invention will become further apparent upon consideration of the following description taken in conjunction with the accompanying drawings, wherein.

DETAILED DESCRIPTION OF THE INVENTION

Figure 1:
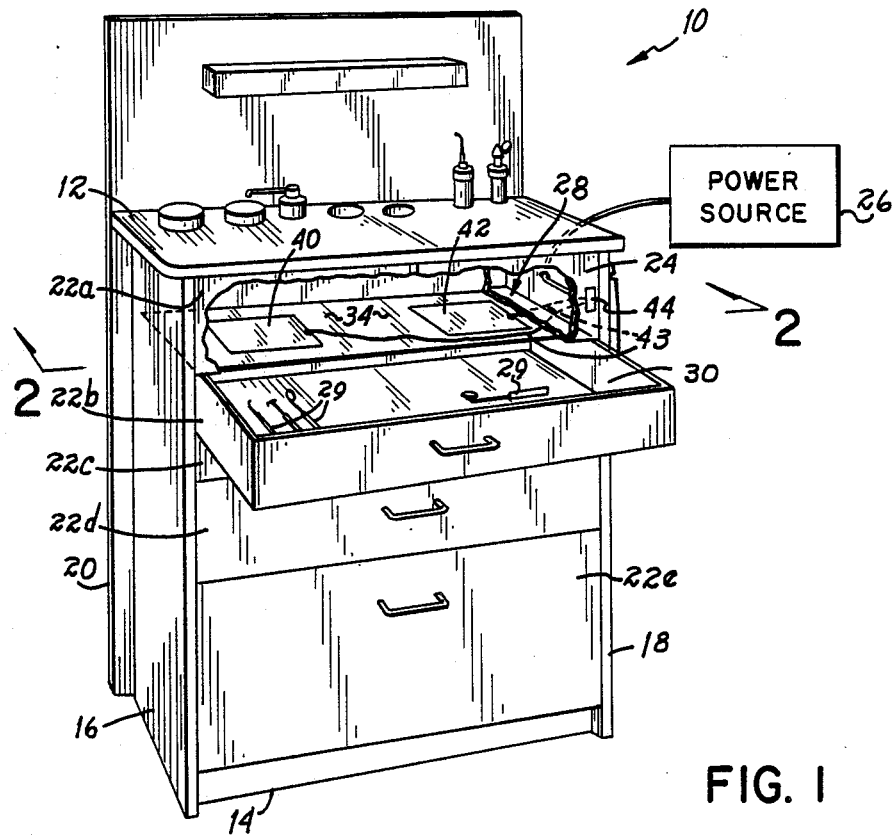
FIG. 1 is a perspective view of a treatment cabinet having a portion cut away to illustrate the instrument heating device of this invention.
Figure 2:
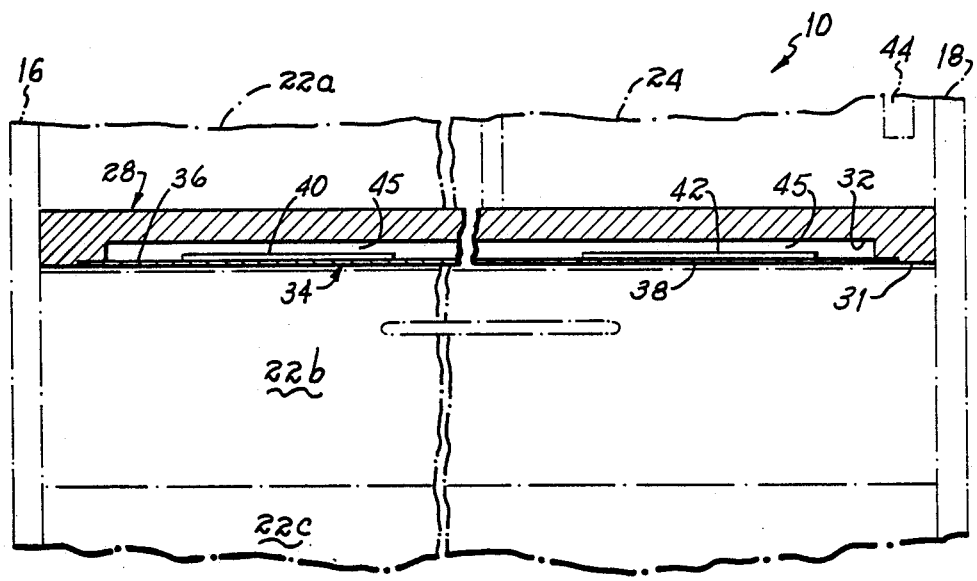
FIG. 2 is an elevational view in partial cross section taken generally along line 2—2 of FIG. 1.

Referring now to FIGS. 1 and 2, a treatment cabinet 10 is illustrated for use in the examination rooms of dentists, otolaryngologists or other health care professionals. The cabinet 10 comprises a top 12, bottom 14, opposed side walls 16, 18 and a back wall 20. In the illustrated embodiment, the cabinet 10 supports five drawers 22a–e from the top 12 to the bottom 14. A control panel 24 is mounted to the cabinet 10 adjacent the uppermost drawer 22a which is connected to a source of power such as a wall socket illustrated schematically in FIG. 1 with a reference number 26.

A support plate or ledge 28 is mounted to the side walls 16 and 18 of the cabinet 10 at the bottom of the uppermost drawer 22a and the control panel 24. This ledge 28 faces the interior 30 of an instrument drawer 22b located immediately beneath the ledge 28 within which a variety of instruments 29 are stored.

The ledge 28 is formed with a rectangular-shaped recess 32 which extends across substantially the entire surface area of the underside 31 of ledge 28. This recess 32 mounts a heat conductive plate 34 having a top surface 36 facing the ledge 28 and a bottom surface 38 facing the interior 30 of instrument drawer 22b. In the presently preferred embodiment, the plate is formed of black anodized aluminum or some other highly heat conductive material. A pair of heating elements 40 and 42 are mounted to the top surface 36 of the heat conductive plate 34 so that they are located within the recess 32 in ledge 28 with the heat conductive plate 34 mounted therein. Preferably, an air space 45 is formed within the recess 32 between the top surface of heating elements 40, 42 and the ledge 28. The heating elements 40, 42 are connected in series by leads 43 to a switch 44 which opens and closes an electrical circuit supplied with power from the source 26.

In one presently preferred embodiment of this invention, the interior 30 of instrument drawer 22b has a width of about 22.875 inches, a depth of about 12.1875 inches and a height of about 2.25 inches. The heat conductive plate 34 is about 0.0625 inches thick and is carried within the recess 32 of the ledge 28 so that its bottom surface 38 is flush with the underside 31 of the ledge 28. The heat conductive plate is preferably about 12 inches deep and about 20 to 22 inches wide. Each of the heating elements 40, 42 is about 4 inches deep, 8 inches wide and has a thickness of about 0.0625 inches so that an air gap 45 of about 0.25 inches is formed in the recess 32 between the top surface of the heating elements 40, 42 and the ledge 28. Each heating element 40, 42 has a power rating of 80 watts at 115 volts ac and the heating elements 40, 42 are preferably wired in series so that their combined power output is 40 watts at 115 volts ac.

Under these conditions, the heating elements 40, 42 are effective to heat the heat conductive plate 34 to a temperature of about 145° F. In turn, the heat conductive plate 34 heats the interior 30 of instrument drawer 22b to a temperature above body temperature and preferably about 115° F. The heat loss by radiation and convection from both the heating elements 40, 42 and heat conductive plate 34 is sufficient to limit the temperature within the interior 30 of instrument drawer 22b to a constant 115° without the use of any form of temperature regulation. The physician or dentist merely turns the switch 44 on to energize the heating elements 40, 42, and no further adjustment is required.

While the invention was described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. Apparatus for warming medical or dental examination instruments housed in the interior of an instrument drawer of a treatment cabinet having a horizontal support located above the instrument drawer, said apparatus comprising:

a heat conductive plate recessed within a horizontal support of a treatment cabinet immediately above the interior of the instrument storage drawer thereof to concentrate heat within the interior of the drawer;

heating means mounted to said heat conductive plate for heating said plate to a temperature such that examination instruments stored within the interior of the instrument drawer are heated to a temperature which is above body temperature but less than that which would cause discomfort in examining a patient.

2. The apparatus of claim 1 in which said heat conductive plate is recessed within the ledge located above the instrument drawer of the treatment cabinet.

3. The apparatus of claim 1 in which said heat conductive plate is formed of black anodized aluminum.

4. The apparatus of claim 1 in which said heating means comprises two flat heating elements connected in series, said heating elements having sufficient power to heat said heat conductive plate so that the interior of the instrument drawer and instruments stored therein are heated to a temperature of about 115° F.

5. The apparatus of claim 1 in which said heat conductive plate has a first surface which faces the horizontal support of the treatment cabinet and a second surface which faces the interior of the drawer, said heating means being mounted to said first surface of said heat conductive plate.

6. Apparatus for storing and heating medical or dental examination instruments, comprising:
   a treatment cabinet having an interior formed by a top wall, a bottom wall, opposed side walls and a back wall, said opposed side walls supporting a number of drawers within said interior of said treatment cabinet including an instrument drawer located immediately beneath a horizontal support fixedly mounted to said cabinet;
   a heat conductive plate recessed within said horizontal support of said cabinet immediately above said instrument drawer, said heat conductive plate having a first surface facing said horizontal support and a second surface facing the interior of said instrument drawer to concentrate heat within the interior of the instrument drawer;
   at least one heating element mounted to one of said first surface and said second surface of said heat conductive plate;
   means for supplying power to said at least one heating element for heating said heat conductive plate to a temperature which warms instruments stored within said interior of said instrument drawer to a temperature above body temperature but less than that which would cause discomfort in examining a patient.

7. The apparatus of claim 6 in which said ledge of said cabinet is formed with a recess, said heat conductive plate being mounted within said recess of said ledge so that said second surface thereof faces said interior of said instrument drawer.

8. The apparatus of claim 7 in which said at least one heating element is mounted to said first surface of said heat conductive plate within said recess formed in said ledge.

9. The apparatus of claim 8 in which said at least one heating element is spaced from said ledge of said cabinet forming an air gap therebetween within said recess.

10. The apparatus of claim 6 in which said heat conductive plate is formed of black anodized aluminum.

11. The apparatus of claim 6 in which said at least one heating element comprises two flat heating elements connected in series, said heating elements having sufficient power to heat said heat conductive plate so that said interior of said instrument drawer is heated to a temperature of about 115° F.

* * * * *